(12) United States Patent
Omote et al.

(10) Patent No.: US 9,020,101 B2
(45) Date of Patent: Apr. 28, 2015

(54) TARGET FOR X-RAY GENERATOR, METHOD OF MANUFACTURING THE SAME AND X-RAY GENERATOR

(71) Applicant: Rigaku Corporation, Akishima-shi, Tokyo (JP)

(72) Inventors: Kazuhiko Omote, Akiruno (JP); Kazuaki Shimizu, Ibaraki (JP); Naohisa Osaka, Ome (JP)

(73) Assignee: Rigaku Corporation, Akishima (JP)

( * ) Notice: Subject to any disclaimer, the term of this patent is extended or adjusted under 35 U.S.C. 154(b) by 185 days.

(21) Appl. No.: 13/759,686

(22) Filed: Feb. 5, 2013

(65) Prior Publication Data
US 2013/0259207 A1 Oct. 3, 2013

(30) Foreign Application Priority Data
Mar. 27, 2012 (JP) .................................. 2012-071866

(51) Int. Cl.
| | |
|---|---|
| *H01J 35/12* | (2006.01) |
| *H01J 35/16* | (2006.01) |
| *H01J 35/18* | (2006.01) |
| *H05G 1/02* | (2006.01) |
| *H01J 35/32* | (2006.01) |
| *A61B 6/00* | (2006.01) |
| *H01J 35/10* | (2006.01) |

(52) U.S. Cl.
CPC ................. *H01J 35/12* (2013.01); *H01J 35/32* (2013.01); *A61B 6/4488* (2013.01); *H05G 1/02* (2013.01); *H01J 35/105* (2013.01); *H01J 35/108* (2013.01); *H05G 1/025* (2013.01); *H01J 2235/081* (2013.01); *H01J 2235/083* (2013.01)

(58) Field of Classification Search
CPC .......... H01J 35/00; H01J 35/08; H01J 35/12; H01J 35/16; H01J 35/18; H01J 35/32; H01J 35/105; H01J 35/108; H05G 1/02; H05G 1/025; A61B 6/4488
USPC ......... 378/141–144, 119, 121, 127–130, 199, 378/200, 204, 210; 250/423 R, 424, 427, 250/493.1, 496.1, 522.1, 526
See application file for complete search history.

(56) References Cited

U.S. PATENT DOCUMENTS 3,914,633 A * 10/1975 Diemer et al. ................ 378/143
4,455,504 A *  6/1984 Iversen .......................... 313/30
(Continued)

FOREIGN PATENT DOCUMENTS

| JP | A-05-343193 | 12/1993 |
|---|---|---|
| JP | B2-07-060757 |  6/1995 |

(Continued)

*Primary Examiner* — Anastasia Midkiff
(74) *Attorney, Agent, or Firm* — Oliff PLC (57) ABSTRACT

There is provided a target for an X-ray generator, including: a holder part made of an electrically conductive material and having an opening part; a diamond plate air-tightly joined to the holder part so as to close the opening part; a thin film target provided on a surface of the diamond plate, with its outer peripheral part extending to the holder part to be electrically connected to the holder part, wherein the holder part is configured to be electrically connected to a power supply of the X-ray generator, and the diamond plate is incorporated into the X-ray generator with one side disposed in a vacuum atmosphere where the thin film target is formed, and an opposite side thereto disposed at a side where the diamond plate is brought into thermal contact with a refrigerant and cooled.

12 Claims, 6 Drawing Sheets

(56) References Cited

U.S. PATENT DOCUMENTS

| | | | |
|---|---|---|---|
| 6,477,233 B1* | 11/2002 | Ribbing et al. | 378/136 |
| 2007/0098143 A1* | 5/2007 | Thangamani et al. | 378/130 |
| 2007/0172030 A1* | 7/2007 | Melnychuk et al. | 378/143 |
| 2014/0029725 A1* | 1/2014 | Ueda et al. | 378/62 |

FOREIGN PATENT DOCUMENTS

| | | |
|---|---|---|
| JP | A-08-115798 | 5/1996 |
| JP | A-2002-042705 | 2/2002 |
| WO | WO 2013/031423 A1 | 3/2013 |

* cited by examiner

TARGET FOR X-RAY GENERATOR, METHOD OF MANUFACTURING THE SAME AND X-RAY GENERATOR

BACKGROUND

1. Field of the Invention

The present invention relates to a target for an X-ray generator which is particularly used for generating a high brilliance (intensity) X-ray, a method of manufacturing the same and the X-ray generator.

2. Description of the Related Art

There is a generally known X-ray generator, such as an apparatus using a filament as a cathode and using a target as an anode, wherein the filament is available as a thermal electron source and the target is an object with which electrons collide. A high voltage of several tens of kilo volts is applied between these cathode and anode so that fast electrons collide with the target, to thereby generate an X-ray.

A brilliance level (called X-ray intensity hereafter) capable of generating X-ray, can be given as a most basic performance of the X-ray generator, and various attempts have been made conventionally for increasing the X-ray intensity. In many cases, a value obtained by dividing an applied power (=applied voltage×applied current) by an area of an X-ray generation area (focal point) on the target, is used as a value showing the X-ray intensity, instead of directly indicating the X-ray intensity. This is because the intensity of the generated X-ray is substantially proportionate to the applied power per unit area. In this specification as well, the applied power per unit area is used as a value showing the X-ray intensity.

As mentioned above, X-ray intensity is determined by power applied per unit area of the target. Therefore, the X-ray intensity is increased by increasing the applied power per unit area. One of the keys to increase the applied power is how quickly heat produced by the collision of electrons can be dissipated from the collision area. Accordingly, various attempts focusing on that point have been made conventionally.

In order to dissipate heat efficiently from the collision area, many of the attempts are made to form a small or thin target material so that another material (thermal diffusion material) having a larger thermal conductivity than that of the target material is brought into contact with the target material (for example, see patent document 1). Namely, patent document 1 (Japanese unexamined patent application publication No. 8-115798) describes in paragraphs 0035 to 0036, as "example 1", an example in which a through hole of 0.2 mm diameter is formed in the center of a polycrystalline diamond substrate 2 (heat conductivity 16.9 W/cm·K) having 10 mm diameter and 1 mm thickness, and the through hole is filled with metal Cu to form a target (anticathode 1), then a Cu film is formed on a rear surface, and a side face is brought into contact with a cooling holder 5 (FIG. 2).

Figure 2:
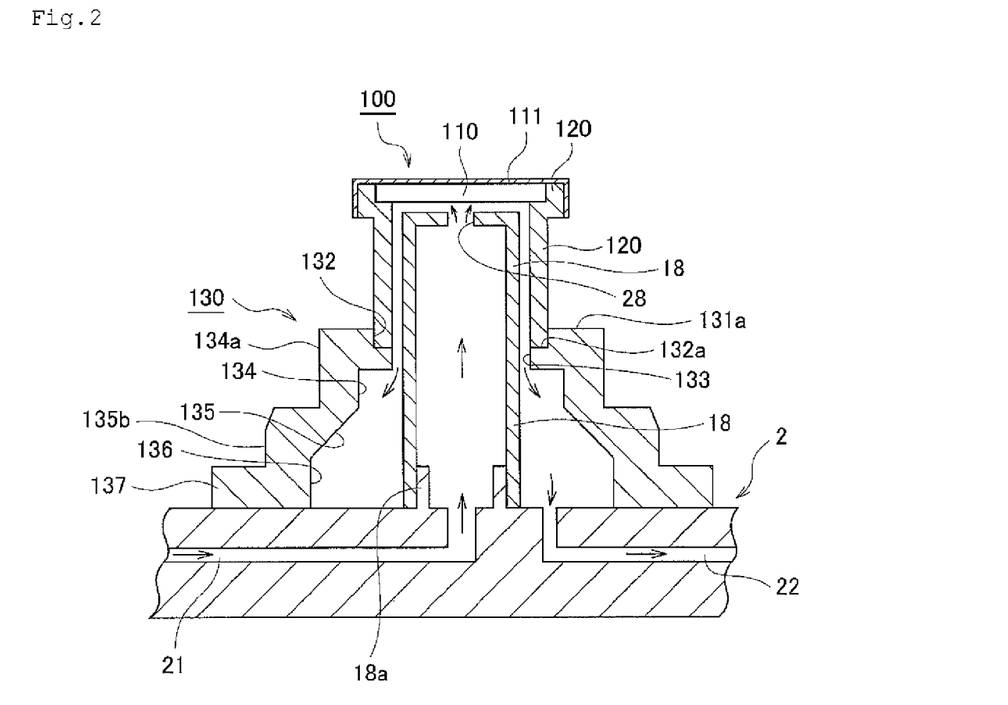
FIG. 2 is a cross sectional view showing the target for an X-ray generator according to the first embodiment of the present invention.

Further, patent document 1 describes an example in paragraph 0044 as a comparative example 1, in which a metal copper film is vapor-deposited on a surface of a disc-shaped polycrystalline diamond substrate 32 having 10 mm diameter and 1 mm thickness to form a thin film target, with a side face in contact with the holder 5 shown in FIG. 2.

RELATED ART DOCUMENTS

Patent Documents

Patent document 1: Japanese unexamined patent application publication No. 8-115798

SUMMARY OF THE INVENTION

In order to generate a high power X-ray, it is necessary to supply electricity of, for example several tens of kilo-volts and several tens of milliamperes to a focus of the target. Here, in case of a target as described in the patent document 1, while the target material which is irradiated with electron beams is electrically conductive, the diamond substrate in contact with the target material is a dielectric material. Therefore, in a case that a small cylindrical target is formed inside the diamond substrate, as described in the patent document 1, a problem of damage to the target may occur because of an inadequate connection of the target to a power supply.

Further, even if the diamond plate with a thin film target formed thereon, is fixed to a conventional target fixing material based on a conventional target supporting method, because there is a large difference in thermal expansion coefficient between the diamond plate and a fixing material, and a temperature is raised, it involves a problem that a stable joint of the diamond plate and the target material is difficult as the X-ray target having a large temperature gradient.

Regarding a system of forming a thin film target on a diamond substrate, some of the documents seem to be at an experimental level yet, due to the above-mentioned difficulty, and almost no practicable technique that can be employed as a commercial product is proposed at present.

Specific means to solve the above problems are described below.

(1) A target for an X-ray generator which is placed inside the X-ray generator and is irradiated with accelerated electrons to generate an X-ray, including:

a holder part made of an electrically conductive material and having an opening part;

a diamond plate air-tightly joined to the holder part so as to close the opening part;

a thin film target provided on a surface of the diamond plate, with its outer peripheral part extending to the holder part to be electrically connected to the holder part, wherein the holder part is configured to be electrically connected to a power supply of the X-ray generator, and the diamond plate is incorporated into the X-ray generator with one side disposed in a vacuum atmosphere where the thin film target is formed, and an opposite side thereto disposed at a side where the diamond plate is brought into thermal contact with a refrigerant and cooled.

(2) The target for an X-ray generator according to the above (1), wherein the diamond plate is incorporated into the X-ray generator with one side disposed in a vacuum atmosphere where the thin film target is formed, and the opposite side thereto disposed at the side where the diamond plate is brought into direct contact with a refrigerant and cooled.

(3) The target for an X-ray generator according to the above (1) or (2), wherein the diamond plate is made of a diamond material having a crystal structure belonging to crystallographic space group Fd3m.

(4) The target for an X-ray generator according to any one of the above (1) to (3), wherein the thin film target is made of an electrically conductive metal material such as Al, Cr, Co, Fe, Ni, Cu, Mo, W, Ag, Au, Rh, Sm, or La.

(5) The target for an X-ray generator according to any one of the above (1) to (4), wherein the diamond plate is a disc plate or an elliptic plate having a thickness of 0.3 mm to 1.5 mm and a diameter of 2 mm to 25 mm.

(6) The target for an X-ray generator according to any one of the above (1) to (5), wherein a base film having a thickness of 1 nm to 40 nm is formed between the thin film target and the diamond plate.

(7) The target for an X-ray generator according to the above (6), wherein the base film is any one of Cr, Ti, V, W and Mo.

(8) The target for an X-ray generator according to any one of the above (1) to (7), wherein a base film having a thickness of 1 nm to 40 nm is formed on the side of the diamond plate opposite to the side where the thin film target is formed, and a corrosion resistant film having a thickness of 5 µm to 10 µm is formed on the base film.

(9) The target for an X-ray generator according to the above (8), wherein the base film is made of any one of Cr, Ti, V, W and Mo, and the corrosion resistant film is made of either one of Au and Cr.

(10) The target for an X-ray generator according to any one of the above (1) to (9), wherein the holder part is formed into a cylindrical shape, the diamond plate is air-tightly joined to the cylindrical holder part so as to close an upper opening part of the cylindrical holder part, and the cylindrical holder part has a deformable property such as not allowing the diamond plate joined to the cylindrical holder part to be destroyed by a difference in thermal expansion between the cylindrical holder part and the diamond plate.

(11) A method of manufacturing the target for an X-ray generator according to any one of the above (1) to (10), including:

forming a thin film target on a surface of the diamond plate by depositing an electrically conductive target substance in an area including the surface of the diamond plate and the surface of the holder part, using a thin film formation method such as ion sputtering, in a state that the diamond plate is joined to the holder part; and forming the thin film target with its outer peripheral part extending to the holder part, so that the thin film target is electrically connected to the holder part.

(12) An X-ray generator wherein the target for an X-ray generator according to any one of the above (1) to (10) is incorporated into the X-ray generator as an X-ray generating target.

According to the above means (1) to (9), the diamond plate is air-tightly joined with the holder part of electrically conductive material so as to close the opening part of the holder part, the thin film target is provided on the surface of the diamond plate, and the outer peripheral part of the thin film target extends upto the holder part to be electrically connected with the holder part, so that power supplying to the X-ray focus is performed in a good manner, even if the thin film target is formed very thin. And by reducing the thickness of the thin film target, heat produced at the target dissipates quickly to the diamond plate having a high thermal conductivity. Further, by cooling the backside of the diamond plate, the heat from the target is radiated outside over the shortest distance. Thus, a stronger X-ray is generated without any substantial problems. Besides, in the above means (2), the diamond plate being cooled in direct thermal contact with the refrigerant is meant to include that the diamond plate is in direct contact with the refrigerant without any intermediates therebetween, and also include that a very thin film exists between the two while substantially the same thermal effect is achieved. According to the above means (10), the holder part is formed in the cylindrical shape, and the cylindrical holder part is malleable to be deformed without destroying the diamond plate which is joined to the cylindrical holder part by a difference in thermal expansion between the cylindrical holder part and the diamond plate, so that the diamond plate is prevented from being destroyed, even when the thickness of the diamond plate is reduced. Thus, further improvement of cooling effect and cost reduction will be achieved.

BRIEF DESCRIPTION OF THE DRAWINGS

FIG. 5(A) is a view showing the surface condition of a Cu bulk target according to the prior art, and FIG. 5(B) is a view showing the surface condition of the target for an X-ray generator according to the first embodiment of the present invention.

DETAILED DESCRIPTION OF THE PREFERRED EMBODIMENTS (A Target for an X-ray Generator According to the First Embodiment)

Figure 1:
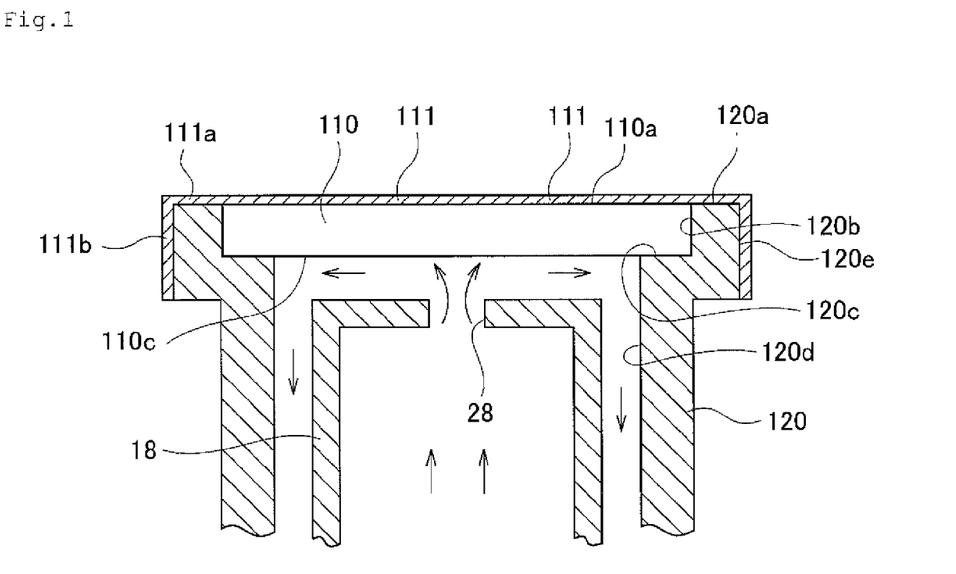
FIG. 1 is an enlarged partial cross sectional view showing the target for an X-ray generator according to a first embodiment of the present invention.
Figure 3:
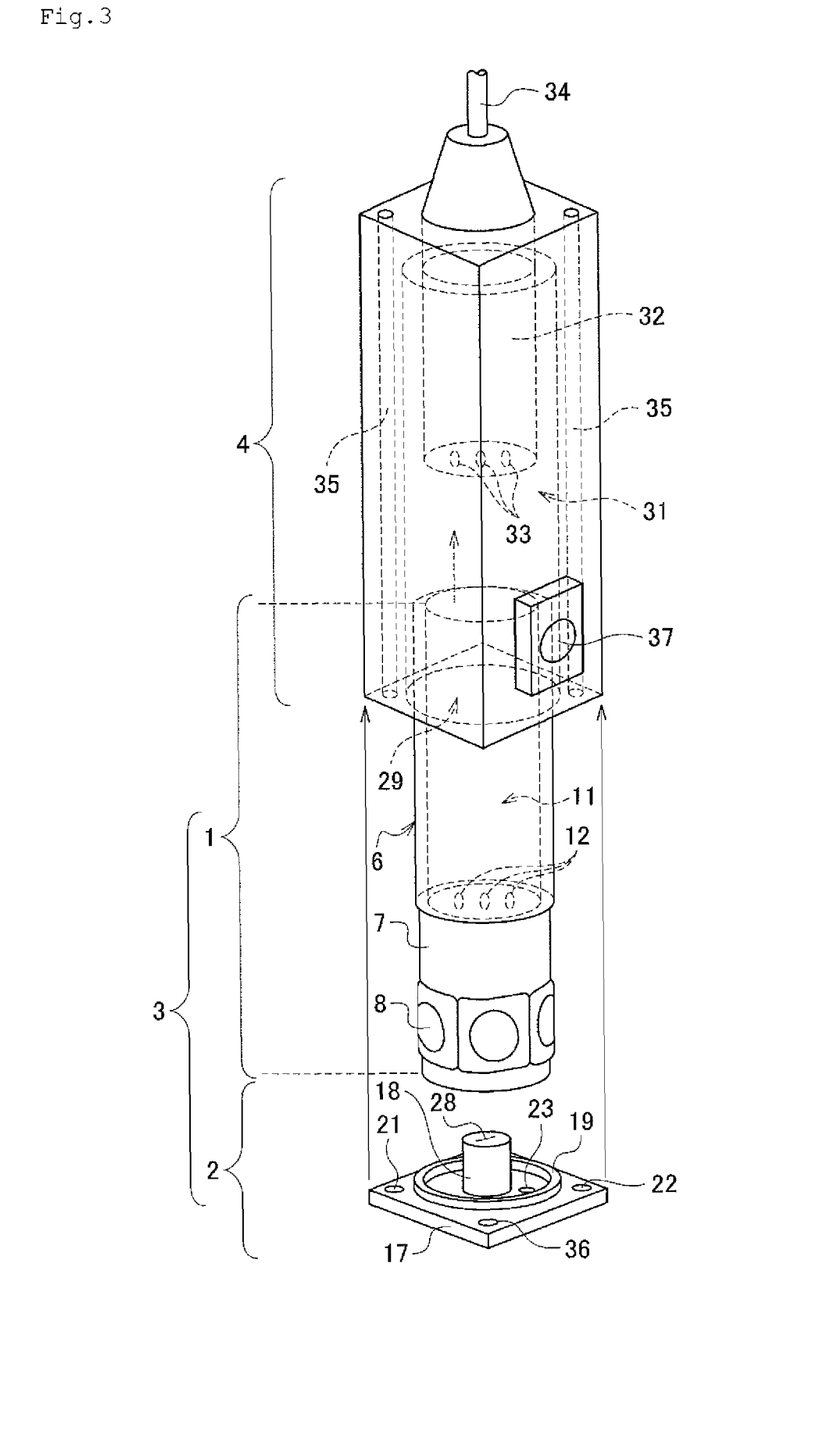
FIG. 3 is an exploded schematic view showing the X-ray generator according to the first embodiment of the present invention.
Figure 4:
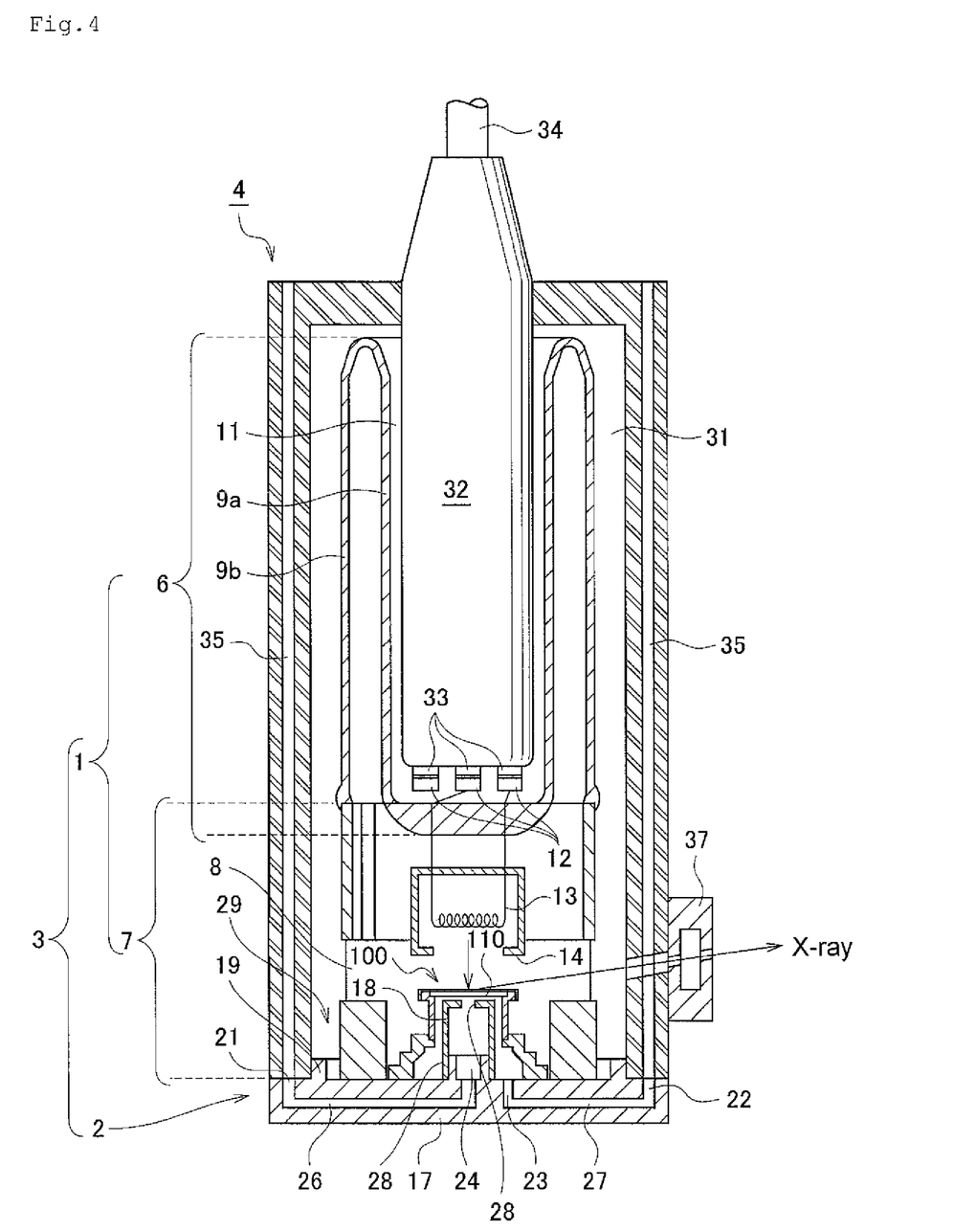
FIG. 4 is a cross sectional view showing the X-ray generator in FIG. 3.

FIG. 1 is an enlarged partial cross sectional view showing the target for an X-ray generator according to the first embodiment of the present invention. FIG. 2 is a cross sectional view showing the target for an X-ray generator according to the first embodiment of the present invention. FIG. 3 is a schematic view showing the X-ray generator according to the first embodiment of the present invention, in an exploded state. FIG. 4 is a cross sectional view of the X-ray generator shown in FIG. 3. Hereinafter, the target for an X-ray generator, the method of manufacturing the target for an X-ray generator, and the X-ray generator according to the embodiments of the present invention will be described with reference to the attached drawings.

Referring to FIGS. 1 and 2, a target 100 for an X-ray generator comprises a diamond plate 110 formed into a shape of a circular plate which is air-tightly joined to a holder part 120 formed in a cylindrical shape from an electrically conductive material, so as to close an upper opening part of the holder part. A thin film target 111 of an electrically conductive material is provided on a surface 110a of the diamond plate 110. Further, a thin film layer forming this thin film target 111 is formed to extend upto a side of the diamond plate 110 and a surface of the holder part 120 to be electrically connected with the holder part 120.

More particularly, the holder part 120 is formed into a cylindrical shape, and at its upper end part is provided with a part having an inner diameter slightly larger than an inner diameter of the cylindrical inner peripheral surface 120d and thereby is formed stepwise. A part extending from an inner peripheral surface 120b of the larger diameter part to an inner peripheral surface of the smaller diameter part or the cylindrical inner peripheral surface 120d is configured as a surface parallel to a plane which is perpendicular to a central axis of the cylindrical shape or at a certain angle θ therefrom to form an upper end surface 120c. A surface at the uppermost position of the cylindrical holder part 120 in the drawings is configured as a surface parallel to a plane which is likewise perpendicular to the central axis of the cylindrical shape or at a certain angle therefrom to form an uppermost end surface 120a. And the inner diameter of the larger diameter part is set almost equal to or slightly larger than the outer diameter of the diamond plate 110. A height of the larger diameter part, or a height of the inner peripheral surface 120b of the larger diameter part or the step is arranged almost equal to the thickness of the diamond plate 110.

The diamond plate 110 is disposed on the upper end surface 120c of the holder part and is air-tightly joined therewith enough to maintain a vacuum atmosphere inside thereof. The joining of these two is performed by any joining method such as brazing or the like. This diamond plate 110 is provided with the thin film target 111 formed on the surface 110a thereof. The thin film layer constituting the thin film target is also formed to extend continuously upto the uppermost end surface 120a of the holder part 120 and an outer peripheral surface 120e of the larger diameter part. Thus, the thin film target 111 is electrically connected with the holder part 120. The formation of the thin film layer is performed, for example by a thin film deposition method such as ion beam sputtering or the like. Further, as will be described later, one side of the diamond plate 110 on which the thin film target 111 is formed is disposed in a vacuum atmosphere, and the back surface 110c side of the diamond plate is set as a refrigerant side (air side).

As shown in FIG. 2, a bottom end part of the holder part 120 is fixed and air-tightly joined to the upper end part of a target support body 130. More precisely, the target support body 130 is a substantially cylindrical pedestal having a diameter which increases stepwise downward. The bottom end part of the holder part 120 is received into a mounting hole 132 formed at the upper end of the support body, and is fixedly connected thereto in air tight manner by, for example, brazing or the like. A smaller diameter part 133 having a diameter slightly smaller than the mounting hole 132 is formed immediate below the mounting hole 132 to provide a step part, a part extending from the mounting hole 132 to the smaller diameter part 133 is configured as a surface parallel to the plane which is perpendicular to the central axis of the cylindrical shape or at a certain angle θ therefrom to form an lower end surface 132a, and the bottom end part of the holder part 120 is air-tightly joined to the lower end surface 132a, for example by brazing or the like. Thus, the holder part 120 and the target support body 130 are electrically connected with each other.

Inside the lower part of the target support body 130, at a part continuing downward from the smaller diameter part 133 is formed a larger diameter part 134, at a part continuing downward from the larger diameter part 134 is formed an diameter expansion part 135 having a diameter which gradually increases downward, and at a part continuing downward from the diameter expansion part 135 is formed a largest diameter part 136. An outer peripheral part of the target support body 130 comprises a part 134a of a small diameter which has a peripheral surface continuing from the upper end surface 131a or the uppermost end surface and corresponds to an inner peripheral area including the mounting hole 132, the smaller diameter part 133 and the larger diameter part 134, and a part 135b of a large diameter which corresponds to an inner peripheral area including the diameter expansion part 135 and further the proximity of a lower end thereof, and below the part is formed a flange part 137.

The flange part 137 will be mounted onto a tube flange 2 of an X-ray tube constituting an X-ray generator (see FIG. 3) which will be described later. An annular protrusion 18a is provided at the center of the tube flange 2, and a cap 18 is fixed to the annular protrusion 18a. The cap 18 is a cylindrical cap having an closed top end and an open bottom end. The closed top end has a slit 28 in the shape of a slit or a narrow aperture formed therein, and an opening of the bottom end is inserted over the annular protrusion 18a to fix it thereto. When the target support body 130 and the cap 18 are fixed to the tube flange 2, the slit 28 of the cap 18 is positioned close to an underside 110c of the diamond plate 110 and opposed thereto.

A coolant passage 26 for introducing water as a refrigerant is connected to inside of the cap 18. Water is introduced through this coolant passage 26 and a jet of water is directed from the slit 28 toward the underside 110c of the diamond plate 110 to cool it. Thereafter, the water flows passing through between the outer peripheral surface of the cap 18 and the inner peripheral surface of the holder part 120, and is discharged outside from a coolant passage 27.

The diamond plate 110 is made of a crystalline diamond produced by a CVD method and having a crystal structure which belongs to the crystallographic space group Fd3m, and has a thermal conductivity of 1,600 W/m K or more. The thin film target 111 is made of a thin film of Cu which is deposited by an ion sputtering method. The diamond plate 110 has an outer diameter of about 9 mm and a thickness of about 500 μm, and the thin film target has a thickness of about 10 μm. The holder part 120 has a thickness of about 0.5 mm. Preferably, the diamond plate 110 has an outer diameter of 4 mm to 25 mm and a thickness of 300 μm to 800 μm, the thin film target has a thickness of 3 μm to 15 μm, and the holder part 120 has a thickness of 0.7 mm to 1.5 mm. More preferably, the diamond plate 110 has an outer diameter of 3 mm to 10 mm and a thickness of 400 μm to 600 μm, the thin film target has a thickness of 8 μm to 12 μm, and desirably the holder part 120 has a thickness of 0.4 mm to 0.6 mm.

Specifically, there is no limitation to a minimum outer diameter of the diamond plate 110, but desirably it is on the order of 4 mm or more because of structural restrictions such as a water cooling structure and the like. If it exceeds 25 mm, because a resistance against vacuum and a pressure of the coolant are exerted in the same direction, there will be a problem that a structure for maintaining its mechanical strength becomes complicated. Also, if the thickness of the diamond plate 110 is less than 300 μm, there will be a problem that the vacuum is not maintained, and if it exceeds 800 μm, another problem of insufficient cooling effect will be caused.

If the thickness of the thin film target is less than 3 μm, there will be a problem that electrons penetrate the target layer and enter into the diamond material of the substrate, and if it exceeds 15 μm, a problem of insufficient heat dissipation of will be caused. If the thickness of the holder part 120 is less than 0.7 mm, a problem of inadequate strength will be caused, and if it exceeds 1.5 mm, there will be a problem that the diamond plate may be damaged by compression stress.

(A Method of Manufacturing the Target for an X-ray Generator According to the First Embodiment)

The target for an X-ray generator is manufactured as described below. First, the holder part 120 formed into a cylindrical shape from an electrically conductive material and the diamond plate 110 are prepared. Next, the diamond plate 110 in the shape of a circular plate is air-tightly joined to the holder part 120 by brazing, so as to close the upper opening of the holder part 120.

Next, in this state of the diamond plate 110 being joined to the holder part, Cu layers are deposited to a thickness of about 5 μm to 14 μm onto the surface 110a of the diamond plate 110, the side 110b of the diamond plate 110, the upper end surface 120c of the holder part, the inner peripheral surface 120b of the larger diameter part of the holder part 120, and the uppermost end surface 120a of the holder part by a vapor deposition method. This deposition is performed using, for example an ion sputtering apparatus maintained at a high vacuum.

Next, the bottom end part of the holder part 120 is airtightly joined, for example by brazing, to the lower end surface 132a of the target support body 130. The target support body 130 to which the target 100 for an X-ray generator in the above mentioned manner is attached is mounted to the tube flange 2 (see FIGS. 2 and 3) of the X-ray tube constituting the X-ray generator which will be described later.

(An X-ray Generator According to the First Embodiment)

FIG. 3 is an exploded schematic view of the X-ray generator according to the first embodiment of the present invention, illustrating an example in which a sealed type X-ray generator is employed. The illustrated sealed type X-ray generator has an X-ray tube 3 comprising a tube main body 1 and the tube flange 2 that are connected to each other, and a tubular shield 4 which houses the entire structure of the tube main body 1 and to which the tube flange 2 is connected. The tubular shield 4 is formed, for example, of brass.

In this embodiment, the tubular shield 4 as one casing part and the tube flange as another casing part are joined together to form one complete casing.

The tube main body 1 comprises a glass tip end part 6, a metal proximal part 7 connected to the tip end part 6, and an X-ray transmission window 8 formed in the case 7 at a proper position thereof. The tip end part 6 has a double glass structure comprising an inner glass wall 9a and an outer glass wall 9b, as shown in FIG. 4, and a cylindrical concavity 11 is formed inside the inner glass wall 9a. And a terminal 23 for power supply is provided at the bottom of the concavity 11.

A surrounding part around the concavity 11 enclosed by the inner glass wall 9a and the outer glass wall 9b, and inside of the proximal part 7 connecting to the surrounding part are air-tightly sealed, and their insides are maintained in a high vacuum state. A filament 13 electric conductively connected with the terminal 12 is provided inside of the proximal part 7, and a wehnelt 14 is provided around the filament 13. The target 100 is provided at a position opposed to the filament 13.

The tube flange 2 connected to the bottom of the proximal part 7 of the tube main body 1 comprises, as shown in FIG. 3, a rectangular base 13 such as a square or an oblong, the cap 18 provided at a center of the base 17, and a fitting protrusion 19 provided in the shape of a circular ring around the cap 18. A slit 28 is formed in the top surface of the cap 18. The base 17 and the cap 18 are formed, for example, of brass.

The base 17 is provided at one corner thereof with a coolant inlet port 21 and at an opposite corner thereof with a coolant outlet port 22. The base 17 is also provided with a coolant recovery port 23 at close to the cap 18. In FIG. 4, the base 17 is provided with a coolant injection port 24 to be located within the cap 18, and this coolant injection port 24 and the coolant inlet port 21 are connected to each other by a coolant passage 26 formed inside the base 17. Also the coolant recovery port 23 and the coolant outlet port 22 are connected to each other by a coolant passage 27 formed inside the base 17.

The X-ray tube 3 is formed by connecting the base 17 of the tube flange 2 to the bottom of the proximal part 7 of the tube main body 1, and the connection is performed by any desired method. For example, a female thread is formed in the bottom of the proximal part 7, a through hole is formed in the base 17 at a position corresponding to the female thread, and a bolt is passed through the through hole and threaded into the female thread, so as to fixedly connect the base 17 to the bottom of the proximal part 7.

In FIG. 3, a circular fitting hole 29 which fits the outer peripheral surface of the fitting protrusion 19 formed on the tube flange 2 is provided in the bottom of the tube shield 4 that houses the tube main body 1 of the X-ray tube 3, and a cylindrical recessed space 31 opening at the fitting hole 29 is formed. This recessed space 31 has an inner diameter slightly larger than an outer diameter of the tube main body 1, and a length longer than a length of the tube main body 1, so that the tube main body 1 is housed within the recessed space 31.

A tubular high voltage relay 32 having high voltage terminals at a tip end thereof is attached to an end of the tube shield 4 opposed to the fitting hole 29. The high voltage terminals 33 are connected with a high voltage cable 34 through which high voltage is applied to the high voltage terminals. Also within the tube shield 4, two coolant passages 35 are provided outside the recessed space 31.

When assembling the X-ray tube 3 and the tube shield 4, in FIG. 3, the tube main body 1 of the X-ray tube 3 is inserted into the recessed space 31 through the opening of the tube shield 4 or the fitting hole 29, to bring the tube flange 2 into contact with the bottom of the tube shield 4. Here, as shown in FIG. 2, the fitting hole 29 of the tube shield 4 fits the outer periphery of the fitting protrusion 19 of the tube flange 2.

Thereafter, the tube flange 2 is fixedly connected to the bottom of the tube shield by a proper connecting method. Any method can be used as this connecting method. For example, in FIG. 3, a through hole 36 is provided at one corner of the base 17 of the tube flange 2, and another through hole (not shown) is also provided at an opposite corner thereof, and further, female threads (not shown) corresponding to these through holes are formed in the bottom of the tube shield 4, and bolts (not shown) passing through the through holes 36 etc. are screwed into the female threads in the bottom of the tube shield 4, so that the tube flange 2 is fixedly connected to the bottom of the tube shield 4, and thereby the X-ray generator as shown in FIG. 4 is assembled.

When the X-ray tube 3 is housed within the recessed space 31 of the tube shield 4, the high voltage terminals 33 on the tube shield 4 side and the terminal 12 on the X-ray tube 3 side are electric conductively connected. When high voltage is supplied through the high voltage cable, the filament 13 is turned on, and high voltage is applied between the filament 13 and the target 100, and also a certain control voltage is applied between the filament and the wehnelt 14. When the base 17 of the tube flange 2 is connected to the bottom of the tube shield 4, the coolant inlet port 21 and the coolant outlet port 22 of the base 17 are connected with the coolant passages 35 of the tube shield 4 respectively.

The filament 13 generates heat when turned on and emits thermal electrons. The emitted thermal electrons are accelerated by the high voltage applied between the filament 13 and the target 100, while being controlled of its travelling direction by the control voltage applied to the wehnelt 13, and collide with the target 100. During this collision, an X-ray is generated from the target 100 and diverges into a wide angular range.

During the generation of X-ray from the target 100, a coolant or cooling water introduced through the coolant inlet port 21 into the coolant passage 26 of the base 17 is injected through the coolant injection port and the slit 28 (in the shape of a slit or a narrow aperture) of the cap 18 toward the backside of the target 100, and thereby preventing the target from being heated to an abnormally high temperature. The cooling water used for the cooling process is collected from the coolant collection port 23 provided near the cap 18 into the coolant passage 27 inside the base 17, and then is discharged through the coolant outlet port 22.

An X-ray shutter 37 which opens and closes an X-ray passage is provided at a proper location close to the bottom of the tube shield 4. The X-ray generated from the target 100 passes through the X-ray transmission window 8 to arrive at the X-ray shutter 37. When the X-ray shutter 37 is set to an open state, the X-ray passes through the X-ray shutter 37 to be taken out to outside. On the other hand, when the X-ray shutter 37 is set to a close state, the X-ray is prevented from being taken out to outside of the tube shield 4.

Figure 5:
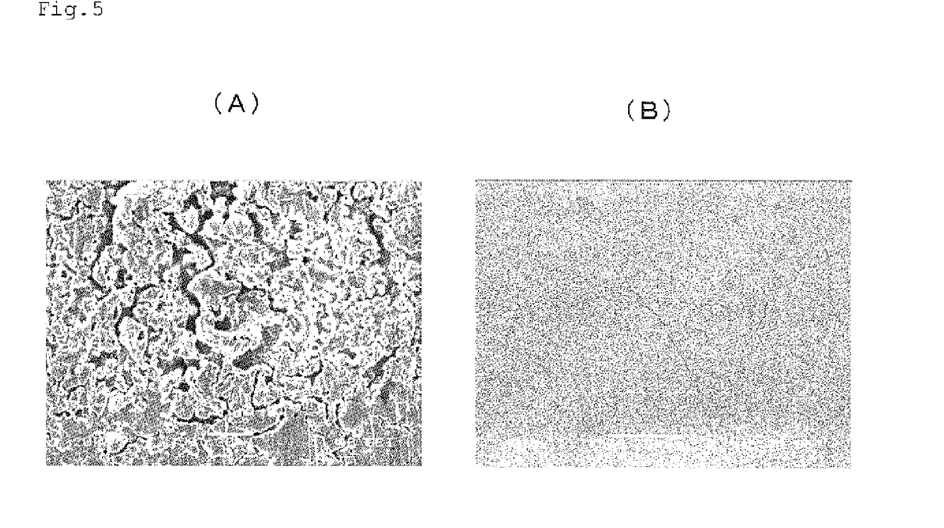
FIG. 5 shows surface conditions of targets after an X-ray generation test, and more particularly

When an electron beam focused into 0.1 mm×1.1 mm (=focus size) continuously irradiated the target 100 for an X-ray generator according to the first embodiment, a stable X-ray was obtained for a long time at a power load of 5.4 kW/mm$^2$. Because a maximum power load for a target depends on a focus size, the above value becomes 40 kW/mm$^2$, when converted into a focus size of 20 μm×80 μm. On the other hand, in case of an ordinary Cu target for which a bulk Cu is used, the above value becomes half or less than that. Further, FIG. 5 shows surface conditions of the target after an X-ray generating test. Particularly, FIG. 5(A) is a surface condition of a conventional Cu bulk target after a power load of 40 kV×11 mA (=440 W=4 kW/mm$^2$) was applied for about one hour, and it is found that the surface is completely damaged. On the other hand, FIG. 5(B) is a surface condition of the target for a X-ray generator according to the first embodiment after a power load of 40 kV×15 mA (=600 W=545 kW/mm$^2$) was applied for about 100 hours, and it is found that the surface maintains a fully normal condition. Besides, in both cases, the focus size was 0.1 mm×1.1 mm.

(A Target for an X-ray Generator According to the Second Embodiment)

Figure 6:
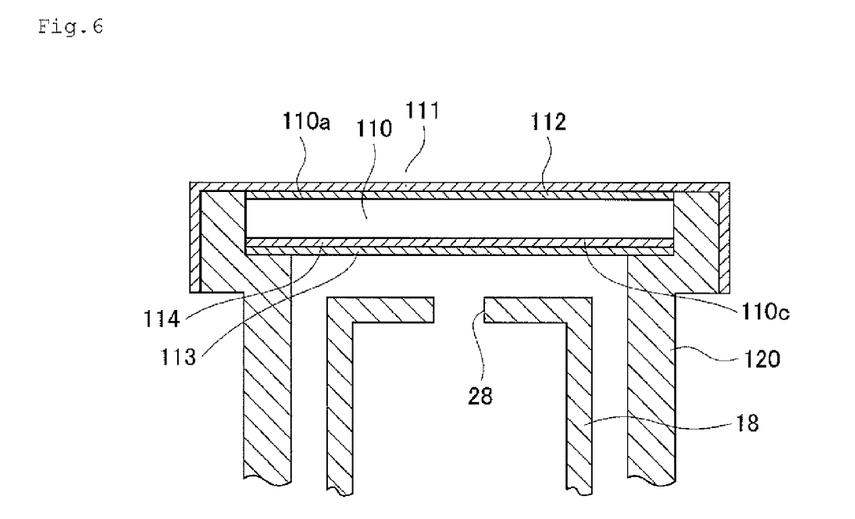
FIG. 6 is an enlarged partial cross sectional view showing a target for an X-ray generator according to a second embodiment of the present invention.

FIG. 6 is a partially enlarged cross sectional view of the target for an X-ray generator according to the second embodiment of the present invention. As shown in FIG. 6, configuration of this embodiment is the same with the first embodiment, except that an base film 112 of Cr film having a thickness of about 10 nm is formed onto the surface of the diamond plate 110, a thin film target 111 similar to that of the first embodiment is formed thereon, and furthermore, another base film 114 is formed onto the backside 110c of the diamond plate 110, and a corrosion resistant film 113 is formed thereon. The base film 114 is a Cr film having a thickness of about 10 nm, and the corrosion resistant film 113 is an Au film having a thickness of 10 μm.

Besides, the base film 112 formed between the thin film target 111 and the diamond plate 110 has a thickness selected appropriately to be in a range of 1 nm to 40 nm, and uses a material of either Cr, Ti, V, W or Mo selected according to the material of the thin film target. The base film 114 formed onto the backside 110c of the diamond plate 110 has a thickness within a range of 1 nm to 40 nm, and uses a material selected appropriately from Cr, Ti, V, W and Mo. Preferably, the corrosion resistant film 113 formed onto the base film 114 is a Au or Cr film having a thickness of 5 μm to 10 μm. According to this embodiment, the formation of the base film 112 makes the bonding of the diamond plate 110 and the thin film target 111 stronger, thus improving the durability. Also, because the base film 114 and the corrosion resistant film 113 are formed onto the backside 110c of the diamond plate 110, the diamond plate 110 is prevented from deteriorating over time due to use of the refrigerant for cooling. Alternatively, only the corrosion resistant film 113 is provided onto the backside 110c of the diamond plate 110, without the base film 114.

Figure 7:
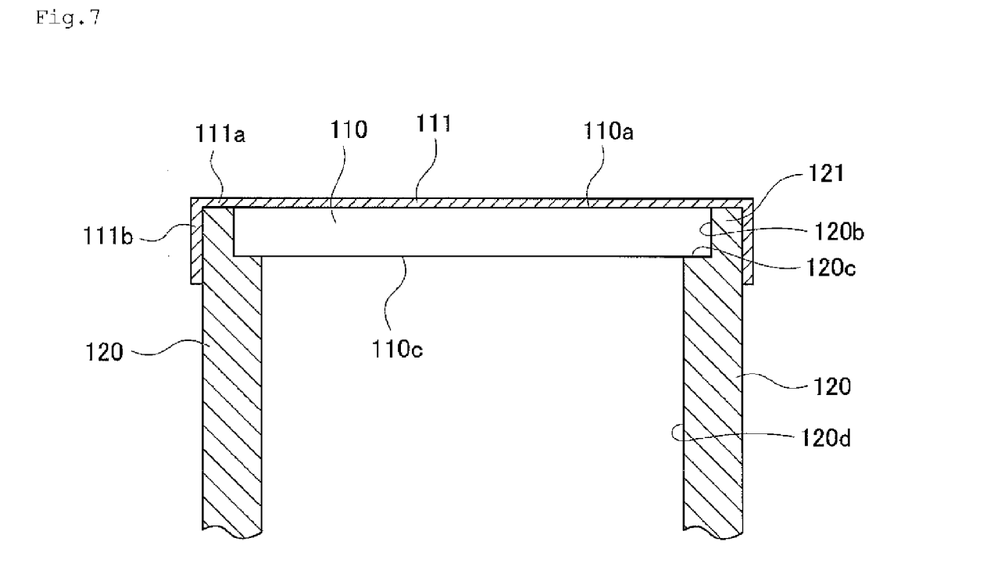
FIG. 7 is an enlarged partial cross sectional view showing a target for an X-ray generator according to a third embodiment of the present invention.

FIG. 7 is a partially enlarged cross sectional view of the target for an X--ray generator according to the third embodiment. As shown in FIG. 7, configuration of this embodiment is the same with the first embodiment, except that the inner periphery of the cylindrical holder part 120 at the top end thereof is partly removed to form a thin part 121, the diamond plate 110 is placed on and joined to an upper end surface 120c which is formed by providing the thin part 121. This embodiment has an advantage that the holder part 120 is easily manufactured only by removing a part of the inner periphery of the cylindrical body at the upper end thereof by machining.

Figure 8:
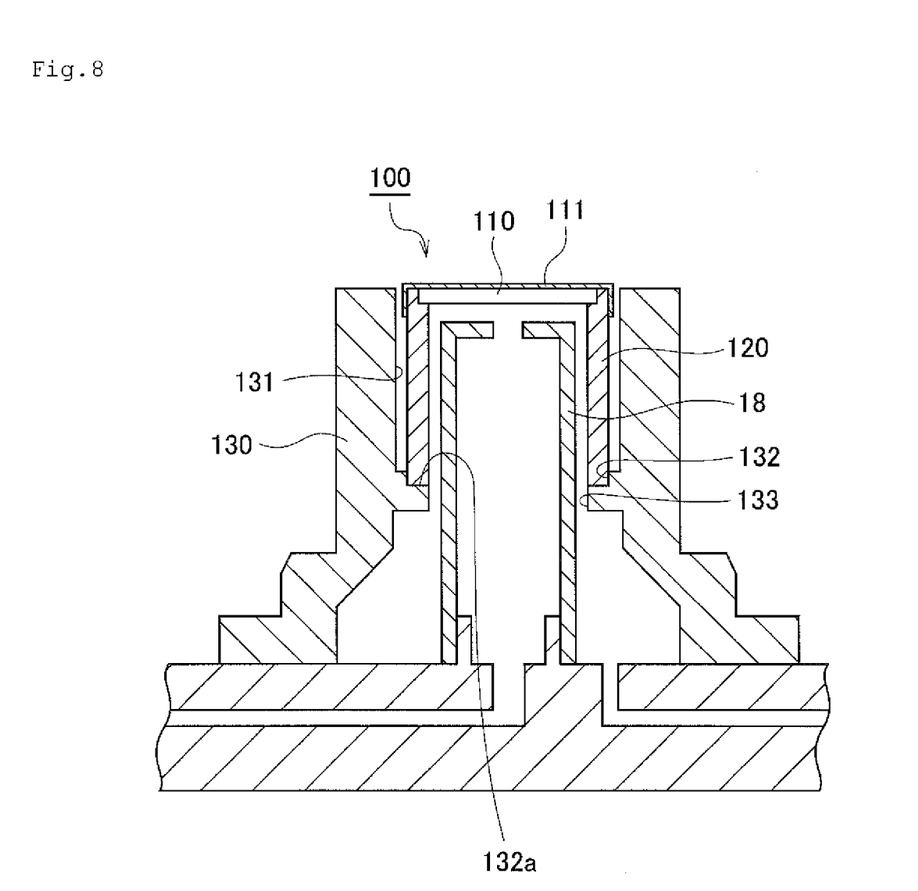
FIG. 8 is a cross sectional view showing a target for an X-ray generator according to a fourth embodiment of the present invention.

FIG. 8 is a cross sectional view of the target for an X-ray generator according to the fourth embodiment. Configuration of this embodiment is the same with the third embodiment, except that a target support 130 differs from that of the first embodiment (=the third embodiment). The target support body 130 of this embodiment is provided with a circular hole 131 formed in the cylindrical body to have an inner diameter slightly larger than the outer diameter of the holder part 120, and is provided with a step part by forming a first small diameter part 132 and a second small diameter part 133 having a diameter slightly smaller than that of the first small diameter part in succession at the bottom end of the circular hole, a part extending from the first small diameter part 132 to the second small diameter part 133 is configured as a surface parallel to the plane which is perpendicular to the central axis of the cylindrical body to form an lower end surface 132a, and the bottom end part of the holder part 120 is air-tightly joined to the lower end surface 132a, for example by brazing or the like. This embodiment has advantages that heat capacity of the target support body 130 is increased, so that a heat radiation effect is enhanced, and that the target is surrounded by an electrically conductive body, so that an electric field distribution is improved, and a focus shape of electrons on the target is put in order.

What is claimed is:

1. A target for an X-ray generator which is placed inside the X-ray generator and is irradiated with accelerated electrons to generate an X-ray, comprising:
    a holder part made of an electrically conductive material and having an opening part and a cylindrical shape;
    a diamond plate coupled to the holder part in an air-tight manner so as to close an upper portion of the opening part; and
    a thin film target provided on a surface of the diamond plate, with its outer peripheral part extending to the holder part to be electrically connected to the holder part;
    wherein:
        the holder part is configured to be electrically connected to a power supply of the X-ray generator,
        the diamond plate is incorporated into the X-ray generator with one side disposed in a vacuum atmosphere where the thin film target is formed, and an opposite side thereto disposed at a side where the diamond plate is brought into thermal contact with a refrigerant and cooled, and
        the holder part is deformable, preventing a difference in thermal expansion between the holder part and the diamond plate from destroying the diamond plate.

2. The target for an X-ray generator according to claim 1, wherein the diamond plate is incorporated into the X-ray generator with one side disposed in a vacuum atmosphere where the thin film target is formed, and the opposite side thereto disposed at the side where the diamond plate is brought into direct contact with a refrigerant and cooled.

3. The target for an X-ray generator according to claim 1, wherein the diamond plate is made of a diamond material having a crystal structure belonging to crystallographic space group Fd3m.

4. The target for an X-ray generator according to claim 1, wherein the thin film target is made of an electrically conductive metal material.

5. The target for an X-ray generator according to claim 1, herein the diamond plate is a disc plate or an elliptic plate having a thickness of 0.3 mm to 1.5 mm and a diameter of 2 mm to 25 mm.

6. The target for an X-ray generator according to claim 1, in which a base film having a thickness of 1 nm to 40 nm is formed between the thin film target and the diamond plate.

7. The target for an X-ray generator according to claim 6, wherein the base film is any one of Cr, Ti, V, W and Mo.

8. The target for an X-ray generator according to claim 1, wherein a base film having a thickness of 1 nm to 40 nm is formed on the side of the diamond plate opposite to the side where the thin film target is formed, and a corrosion resistant film having a thickness of 5 µm to 10 µm is formed on the base film.

9. The target for an X-ray generator according to claim 8, wherein the base film is made of any one of Cr, Ti, V, W and Mo, and the corrosion resistant film is made of either one of Au and Cr.

10. A method of manufacturing a target for an X-ray generator, comprising:
   forming a holder part having an opening part and a cylindrical shape;
   coupling a diamond plate to the holder part in an air-tight manner so as to close an upper portion of the opening part;
   forming a thin film target on a surface of the diamond plate by depositing an electrically conductive target substance in an area including the surface of the diamond plate and the surface of the holder part, using a thin film deposition method, in a state that the diamond plate is coupled to the holder part; and
   forming the thin film target with its outer peripheral part extending to the holder part, so that the thin film target is electrically connected to the holder part;
   wherein the holder is deformable, preventing a difference in thermal expansion between the holder part and the diamond plate from destroying the diamond plate.

11. An X-ray generator wherein the target for an X-ray generator according to claim 1 is incorporated into the X-ray generator as an X-ray generating target.

12. The target for an X-ray according to claim 4, wherein the thin film is made of Al, Cr, Co, Fe, Ni, Cu, Mo, W, Ag, Au, Rh, Sm, or La.

* * * * *